(12) United States Patent
Yuan

(10) Patent No.: US 10,371,723 B2
(45) Date of Patent: Aug. 6, 2019

(54) CURRENT SENSOR FOR BIOMEDICAL MEASUREMENTS

(71) Applicant: Juanping Yuan, Huizhou (CN)

(72) Inventor: Juanping Yuan, Huizhou (CN)

(73) Assignee: SHENZHEN DANSHA TECHNOLOGY CO., LTD., Shenzhen, Guangdong (CN)

( * ) Notice: Subject to any disclaimer, the term of this patent is extended or adjusted under 35 U.S.C. 154(b) by 39 days.

(21) Appl. No.: 15/849,695

(22) Filed: Dec. 21, 2017

(65) Prior Publication Data

US 2018/0136261 A1    May 17, 2018

(51) Int. Cl.

| | | |
|---|---|---|
| G01R 15/09 | (2006.01) | |
| G01R 19/00 | (2006.01) | |
| H03K 19/173 | (2006.01) | |
| H03K 19/20 | (2006.01) | |
| A61B 5/00 | (2006.01) | |
| A61B 5/04 | (2006.01) | |

(52) U.S. Cl.
CPC ......... *G01R 19/0092* (2013.01); *G01R 15/09* (2013.01); *H03K 19/173* (2013.01); *H03K 19/20* (2013.01); *A61B 5/04* (2013.01); *A61B 5/72* (2013.01)

(58) Field of Classification Search
CPC .. G01R 15/09; G01R 19/0092; H03K 19/173; H03K 19/20; A61B 5/04; A61B 5/72
USPC ........ 324/219–252, 200, 207.2–207.24, 500, 324/521, 529–530, 750.12, 750.21, 324/754.17, 754.29, 600, 617, 622, 683, 324/709, 76.11, 76.52–76.77, 86, 107, 324/138; 438/73, 3; 73/514.31, 514.39, 73/520.01, 779, 862.193, 862.333
See application file for complete search history.

(56) References Cited

U.S. PATENT DOCUMENTS

2012/0146608 A1 * 6/2012 Wan ..................... H02M 3/156
323/284
2014/0292318 A1 * 10/2014 Wang .................... B82Y 25/00
324/228

* cited by examiner

*Primary Examiner* — Melissa J Koval
*Assistant Examiner* — Trung Nguyen

(57) ABSTRACT

A current sensor for biomedical measurements includes: a first amplifier; a first capacitor; a second capacitor; a first switch connected in parallel with the first capacitor; a second switch connected in parallel with the second capacitor; a second amplifier; a third capacitor; a resistor; and a switched capacitor network. The first capacitor and the second capacitor are connected in series and across a first input and output of the first amplifier. The third capacitor and the resistor are respectively connected across a first input and output of the second amplifier. The switched capacitor network is connected between the output of the first amplifier and the first input of the second amplifier.

12 Claims, 2 Drawing Sheets

CURRENT SENSOR FOR BIOMEDICAL MEASUREMENTS

FIELD OF THE PATENT APPLICATION

The present patent application generally relates to electronic circuits and more specifically to a current sensor for biomedical measurements.

BACKGROUND

In biomedical or electrochemical measurements, the parameters to be measured typically vary cross orders of magnitude. Also, the biomedical or electrochemical processes to be measured are typically highly non-linear. As a result, these measurements demand the measuring circuit, which is typically a current sensing circuit or a current sensor, to have a dynamic range as wide as possible. The nature of biomedical or electrochemical measurements also demands the measuring circuit to be essentially low noise so that the measurement resolution above an acceptable level can be achieved. However, conventional current sensing circuits generally suffer low dynamic range or high noise introduced by offset or feedback mechanisms present in those current sensing circuits.

SUMMARY

The present patent application is directed to a current sensor for biomedical measurements. In one aspect, the current sensor for biomedical measurements includes: a first amplifier; a first capacitor; a second capacitor; a first switch connected in parallel with the first capacitor; a second switch connected in parallel with the second capacitor; a second amplifier; a third capacitor; a resistor; and a switched capacitor network. The first capacitor and the second capacitor are connected in series and across a first input and output of the first amplifier. The third capacitor and the resistor are respectively connected across a first input and output of the second amplifier. The switched capacitor network is connected between the output of the first amplifier and the first input of the second amplifier.

The current sensor for biomedical measurements may further include: a first comparator; a second comparator; an OR gate; a first flip-flop; a second flip-flop; and a third flip-flop. A first input of the first comparator and a first input of the second comparator are connected with the output of the first amplifier. Outputs of the first comparator and the second comparator are connected to inputs of the OR gate respectively, and to clock ports of the first flip-flop and the second flip-flop. Output of the OR gate is connected to clock port of the third flip-flop. D port of each of the first flip-flop, the second flip-flop, and the third flip-flop are connected with $\overline{Q}$ port of the flip-flop.

The switched capacitor network may include a fourth capacitor, a fifth capacitor, a third switch connected in parallel with the fourth capacitor, and a fourth switch connected in parallel with the fifth capacitor, the fourth capacitor and the fifth capacitor being connected in series and connected between the output of the first amplifier and the first input of the second amplifier.

The first switch and the fourth switch may be controlled by a first clock; and the second switch and the third switch may be controlled by a second clock that is complementary to the first clock. The first clock may be configured to transmit $\overline{Q}$ port of the third flip-flop; and the second clock may be configured to transmit Q port of the third flip-flop.

A second input of the first amplifier and a second input of the second amplifier may be biased at a first reference voltage, a second input of the first comparator may be biased at a second reference voltage, a second input of the second comparator is biased at a third reference voltage, $V2>V1$ and $V2=-V3$.

DETAILED DESCRIPTION

Reference will now be made in detail to a preferred embodiment of the current sensor for biomedical measurements disclosed in the present patent application, examples of which are also provided in the following description. Exemplary embodiments of the current sensor for biomedical measurements disclosed in the present patent application are described in detail, although it will be apparent to those skilled in the relevant art that some features that are not particularly important to an understanding of the current sensor for biomedical measurements may not be shown for the sake of clarity.

Furthermore, it should be understood that the current sensor for biomedical measurements disclosed in the present patent application is not limited to the precise embodiments described below and that various changes and modifications thereof may be effected by one skilled in the art without departing from the spirit or scope of the protection. For example, elements and/or features of different illustrative embodiments may be combined with each other and/or substituted for each other within the scope of this disclosure.

Figure 1:
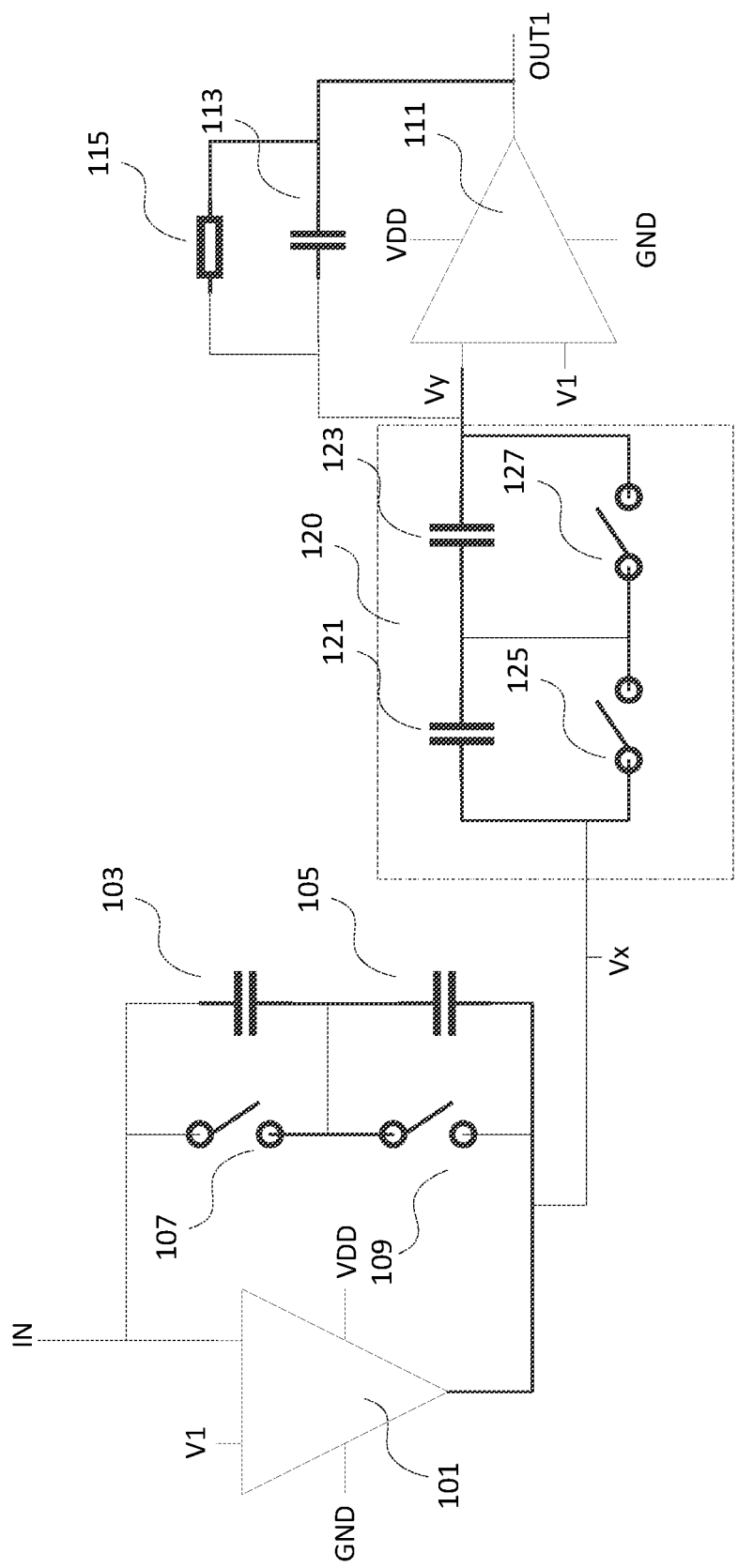
FIG. 1 is a schematic circuit diagram of a portion of a current sensor for biomedical measurements in accordance with an embodiment of the present patent application.

FIG. 1 is a schematic circuit diagram of a portion of a current sensor for biomedical measurements in accordance with an embodiment of the present patent application. Referring to FIG. 1, the current sensor for biomedical measurements includes a first amplifier 101, a first capacitor 103, a second capacitor 105, a first switch 107 connected in parallel with the first capacitor 103, a second switch 109 connected in parallel with the second capacitor 105, a second amplifier 111, a third capacitor 113, a resistor 115, and a switched capacitor network 120.

The first capacitor 103 and the second capacitor 105 are connected in series and across a first input (IN) and the output (Vx) of the first amplifier 101. The third capacitor 113 and the resistor 115 are respectively connected across a first input (Vy) and the output (OUT1) of the second amplifier 111.

The switched capacitor network 120 is connected between the output (Vx) of the first amplifier 101 and the first input (Vy) of the second amplifier 111. The switched capacitor network 120 includes a fourth capacitor 121, a fifth capacitor 123, a third switch 125 connected in parallel with the fourth capacitor 121, and a fourth switch 127 connected in parallel with the fifth capacitor 123. The fourth capacitor 121 and the fifth capacitor 123 are connected in series and connected between the output (Vx) of the first amplifier 101 and the first input (Vy) of the second amplifier 111.

Figure 2:
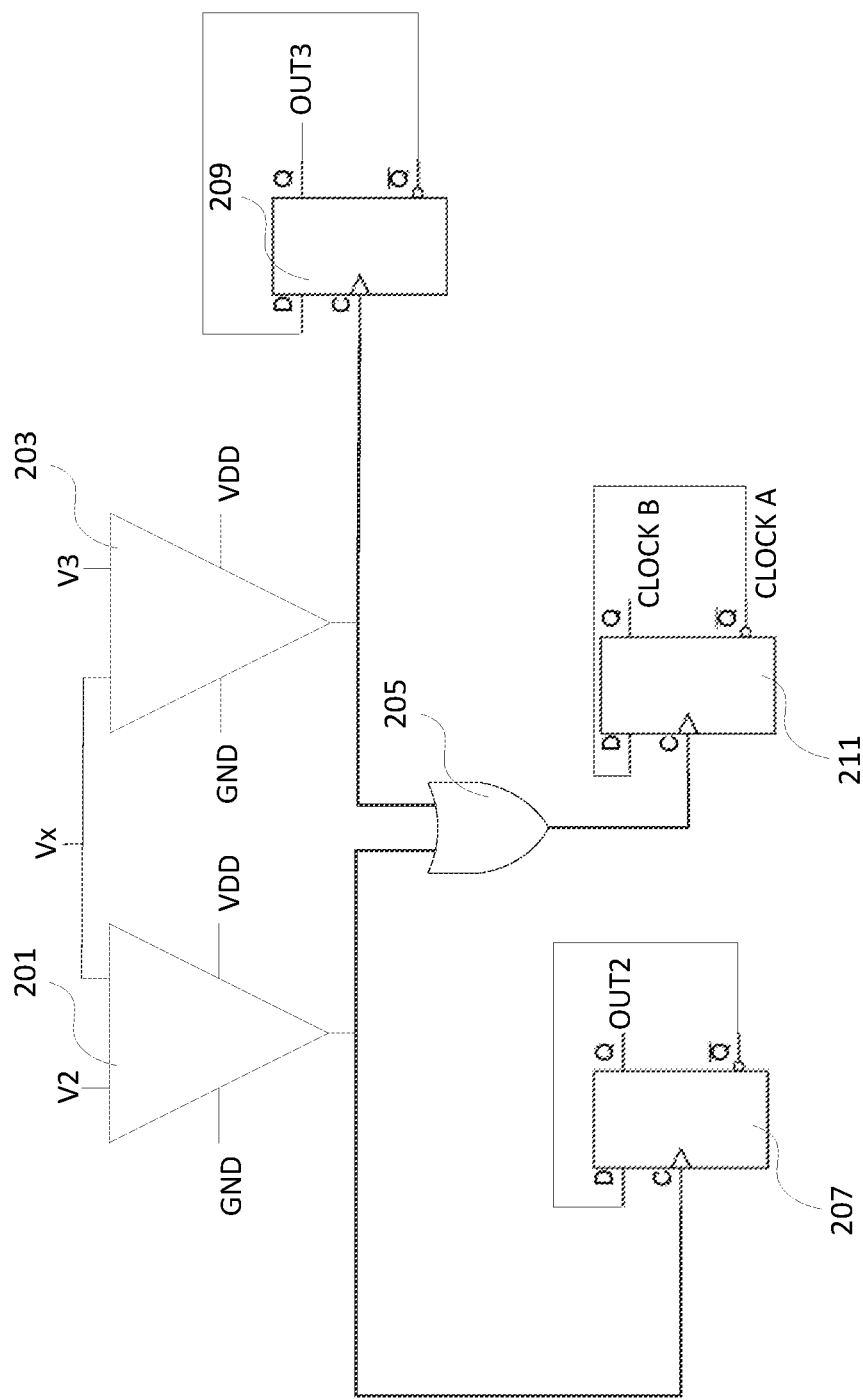
FIG. 2 is a schematic circuit diagram of another portion of the current sensor for biomedical measurements as depicted in FIG. 1.

FIG. 2 is a schematic circuit diagram of another portion of the current sensor for biomedical measurements as depicted in FIG. 1. Referring to FIG. 2, this portion of the current sensor circuit includes a first comparator 201, a second comparator 203, an OR gate 205, a first flip-flop 207, a second flip-flop 209, and a third flip-flop 211. A first input of the first comparator 201 and a first input of the second comparator 203 are connected with the output (Vx) of the first amplifier 101. The outputs of the first comparator 201 and the second comparator 203 are connected to inputs of the OR gate 205 respectively, and to clock ports of the first flip-flop 207 and the second flip-flop 209. The output of the OR gate 205 is connected to the clock port of the third flip-flop 211. For each of the first flip-flop 207, the second flip-flop 209, and the third flip-flop 211, D port of flip-flop is connected with $\overline{Q}$ port of the flip-flop.

In this embodiment, a second input of the first amplifier 101 and a second input of the second amplifier 111 are biased at a first reference voltage V1. A second input of the first comparator 201 is biased at a second reference voltage V2. A second input of the second comparator 203 is biased at a third reference voltage V3. In this embodiment, V2>V1 and V2=−V3.

The first switch 107 and the fourth switch 127 are controlled by a first clock A. The second switch 109 and the third switch 125 are controlled by a second clock B. The second clock B is complementary to the first clock A. In this embodiment, $\overline{Q}$ port (CLOCK A) of the third flip-flop 211 is configured to transmit the first clock A. Q port (CLOCK B) of the third flip-flop 211 is configured to transmit the second clock B.

When the first clock A is high ("1"), and the second clock B is low ("0"), the first switch 107 is closed while the second switch 109 is open. Therefore, the first capacitor 103 is reset while the second capacitor 105 is charging. In the same period, the fourth switch 127 is closed while the third switch 125 is open. Therefore, the fifth capacitor 123 is reset while the fourth capacitor 121 is charging.

When the first clock A is low ("0"), and the second clock B is high ("1"), the first switch 107 is open while the second switch 109 is closed. Therefore, the first capacitor 103 is charging while the second capacitor 105 is reset. In the same period, the fourth switch 127 is open while the third switch 125 is closed. Therefore, the fifth capacitor 123 is charging while the fourth capacitor 121 is reset.

In the aforementioned charge conserving configuration, electrical charges for charging the capacitors 103, 105, 121, 123 are locally provided instead of being provided by the amplifiers 101 and 111. The operations of the capacitors are much faster than the settling time of the amplifiers. Therefore, reset transients and recovery time of the circuit are minimized.

The output (OUT1) of the second amplifier 111 is a first output port of the current sensor for biomedical measurements, and is configured to output a voltage that is linearly related to the current $I_{IN}$ at the first input (IN). More specifically, $V_{OUT1}=V_1+C_1 \cdot I_{IN}$, where $C_1$ is a constant determined by the first, second, fourth, fifth capacitors 103, 105, 121, 123 and the resistor 115.

The Q port (OUT2) of the first flip-flop 207 or the Q port (OUT3) of the second flip-flop 209 is configured to output a digital signal with a frequency being proportional to the current $I_{IN}$ at the first input (IN), depending on the direction of the current $I_{IN}$. More specifically, the output (Vx) of the first amplifier 101 periodically increases linearly with time until it reaches V2 or V3. When Vx reaches V2 or V3, the first comparator 201 or the second comparator 203 is configured to output a digital "1", which inverts the output at the ports CLOCK A, CLOCK B, and OUT2 (or OUT3) and resets Vx to zero. Within each period, the rate at which the output (Vx) of the first amplifier 101 increases with time is proportional to $I_{IN}$, therefore, the frequency of the signal output by OUT2 (or OUT3) is proportional to $I_{IN}$. The Q port (OUT2) of the first flip-flop 207 and the Q port (OUT3) of the second flip-flop 209 thus serve as a second and a third output ports of the current sensor for biomedical measurements.

In this embodiment, for the current $I_{IN}$ that is relatively small and of higher frequency, the output (OUT1) of the second amplifier 111, as the first output port of the current sensor, provides a measurement of the current with relatively low noise. For a relatively large current $I_{IN}$, the second or the third output port of the current sensor for biomedical measurements provides a frequency output that is proportional to the current $I_{IN}$. Therefore, the dynamic range of the current sensor for biomedical measurements is greatly widened. In addition, the current sensor for biomedical measurements provided by the embodiment does not require any external reset clock or sample clock, and therefore bandwidth of the current sensor is not limited by any sample rate.

While the present patent application has been shown and described with particular references to a number of embodiments thereof, it should be noted that various other changes or modifications may be made without departing from the scope of the present invention.

What is claimed is:

1. A current sensor for biomedical measurements comprising:
   a first amplifier;
   a first capacitor;
   a second capacitor;
   a first switch connected in parallel with the first capacitor;
   a second switch connected in parallel with the second capacitor;
   a second amplifier;
   a third capacitor;
   a resistor;
   a switched capacitor network;
   a first comparator;
   a second comparator;
   an OR gate;
   a first flip-flop;
   a second flip-flop; and
   a third flip-flop; wherein:
   the first capacitor and the second capacitor are connected in series and across a first input and output of the first amplifier;
   the third capacitor and the resistor are respectively connected across a first input and output of the second amplifier;
   the switched capacitor network is connected between the output of the first amplifier and the first input of the second amplifier;
   the switched capacitor network comprises a fourth capacitor, a fifth capacitor, a third switch connected in parallel with the fourth capacitor, and a fourth switch connected in parallel with the fifth capacitor, the fourth capacitor and the fifth capacitor being connected in series and connected between the output of the first amplifier and the first input of the second amplifier;
   a first input of the first comparator and a first input of the second comparator are connected with the output of the first amplifier;
   outputs of the first comparator and the second comparator are connected to inputs of the OR gate respectively, and to clock ports of the first flip-flop and the second flip-flop;

output of the OR gate is connected to clock port of the third flip-flop;

D port of each of the first flip-flop, the second flip-flop, and the third flip-flop are connected with $\overline{Q}$ port of the flip-flop;

the first switch and the fourth switch are controlled by a first clock;

the second switch and the third switch are controlled by a second clock that is complementary to the first clock;

$\overline{Q}$ port of the third flip-flop is configured to transmit the first clock; and Q port of the third flip-flop is configured to transmit the second clock.

2. The current sensor for biomedical measurements of claim 1, wherein a second input of the first amplifier and a second input of the second amplifier are biased at a first reference voltage, a second input of the first comparator is biased at a second reference voltage, a second input of the second comparator is biased at a third reference voltage, V2>V1 and V2=−V3.

3. A current sensor for biomedical measurements comprising:
   a first amplifier;
   a first capacitor;
   a second capacitor;
   a first switch connected in parallel with the first capacitor;
   a second switch connected in parallel with the second capacitor;
   a second amplifier;
   a third capacitor;
   a resistor; and
   a switched capacitor network; wherein:
   the first capacitor and the second capacitor are connected in series and across a first input and output of the first amplifier;
   the third capacitor and the resistor are respectively connected across a first input and output of the second amplifier; and
   the switched capacitor network is connected between the output of the first amplifier and the first input of the second amplifier.

4. The current sensor for biomedical measurements of claim 3 further comprising: a first comparator; a second comparator; an OR gate; a first flip-flop; a second flip-flop; and a third flip-flop, wherein a first input of the first comparator and a first input of the second comparator are connected with the output of the first amplifier; outputs of the first comparator and the second comparator are connected to inputs of the OR gate respectively, and to clock ports of the first flip-flop and the second flip-flop; output of the OR gate is connected to clock port of the third flip-flop; and D port of each of the first flip-flop, the second flip-flop, and the third flip-flop are connected with $\overline{Q}$ port of the flip-flop.

5. The current sensor for biomedical measurements of claim 3, wherein the switched capacitor network comprises a fourth capacitor, a fifth capacitor, a third switch connected in parallel with the fourth capacitor, and a fourth switch connected in parallel with the fifth capacitor, the fourth capacitor and the fifth capacitor being connected in series and connected between the output of the first amplifier and the first input of the second amplifier.

6. The current sensor for biomedical measurements of claim 4, wherein the first switch and the fourth switch are controlled by a first clock; and the second switch and the third switch are controlled by a second clock that is complementary to the first clock.

7. The current sensor for biomedical measurements of claim 6, wherein the first clock is configured to transmit $\overline{Q}$ port of the third flip-flop; and the second clock is configured to transmit Q port of the third flip-flop.

8. The current sensor for biomedical measurements of claim 4, wherein a second input of the first amplifier and a second input of the second amplifier are biased at a first reference voltage, a second input of the first comparator is biased at a second reference voltage, a second input of the second comparator is biased at a third reference voltage, V2>V1 and V2=−V3.

9. A current sensor for biomedical measurements comprising:
   a first amplifier;
   a first capacitor;
   a second capacitor;
   a first switch connected in parallel with the first capacitor;
   a second switch connected in parallel with the second capacitor;
   a second amplifier;
   a third capacitor;
   a resistor;
   a switched capacitor network;
   a first comparator; a second comparator;
   an OR gate;
   a first flip-flop;
   a second flip-flop; and
   a third flip-flop; wherein:
   the first capacitor and the second capacitor are connected in series and across a first input and output of the first amplifier;
   the third capacitor and the resistor are respectively connected across a first input and output of the second amplifier;
   the switched capacitor network is connected between the output of the first amplifier and the first input of the second amplifier;
   a first input of the first comparator and a first input of the second comparator are connected with the output of the first amplifier;
   outputs of the first comparator and the second comparator are connected to inputs of the OR gate respectively, and to clock ports of the first flip-flop and the second flip-flop;
   output of the OR gate is connected to clock port of the third flip-flop;
   D port of each of the first flip-flop, the second flip-flop, and the third flip-flop are connected with $\overline{Q}$ port of the flip-flop; and
   the switched capacitor network comprises a fourth capacitor, a fifth capacitor, a third switch connected in parallel with the fourth capacitor, and a fourth switch connected in parallel with the fifth capacitor, the fourth capacitor and the fifth capacitor being connected in series and connected between the output of the first amplifier and the first input of the second amplifier.

10. The current sensor for biomedical measurements of claim 9, wherein the first switch and the fourth switch are controlled by a first clock; and the second switch and the third switch are controlled by a second clock that is complementary to the first clock.

11. The current sensor for biomedical measurements of claim 10, wherein the first clock is configured to transmit $\overline{Q}$ port of the third flip-flop; and the second clock is configured to transmit Q port of the third flip-flop.

12. The current sensor for biomedical measurements of claim 9, wherein a second input of the first amplifier and a second input of the second amplifier are biased at a first reference voltage, a second input of the first comparator is biased at a second reference voltage, a second input of the second comparator is biased at a third reference voltage, V2>V1 and V2=−V3.

* * * * *